US006916298B2

United States Patent
VanBrunt et al.

(10) Patent No.: US 6,916,298 B2
(45) Date of Patent: *Jul. 12, 2005

(54) PNEUMATIC CHEST COMPRESSION VEST WITH FRONT PANEL AIR BLADDER

(75) Inventors: Nicholas P. VanBrunt, White Bear Lake, MN (US); Donald J. Gagne, St. Paul, MN (US)

(73) Assignee: Advanced Respiratory, Inc., St. Paul, MN (US)

( * ) Notice: Subject to any disclaimer, the term of this patent is extended or adjusted under 35 U.S.C. 154(b) by 372 days.

This patent is subject to a terminal disclaimer.

(21) Appl. No.: 09/999,377

(22) Filed: Oct. 31, 2001

(65) Prior Publication Data

US 2002/0082531 A1 Jun. 27, 2002

Related U.S. Application Data

(63) Continuation-in-part of application No. 09/387,319, filed on Aug. 31, 1999, now abandoned, and a continuation-in-part of application No. 09/387,312, filed on Aug. 31, 1999, now Pat. No. 6,379,316, and a continuation-in-part of application No. 09/387,339, filed on Aug. 31, 1999, now Pat. No. 6,471,663.

(51) Int. Cl.[7] .............................................. A61H 31/00
(52) U.S. Cl. ......................................... 601/41; 601/44
(58) Field of Search .......................... 601/41–44, 148, 601/149, 151, 152; 128/DIG. 20

(56) References Cited

U.S. PATENT DOCUMENTS

| 402,779 A | 5/1889 | Steinhoff |
|---|---|---|
| 1,367,420 A | 2/1921 | Munter |
| 1,646,590 A | 10/1927 | Mildenberg et al. |
| 2,338,535 A | 1/1944 | Pfleumer |
| 2,354,397 A | 7/1944 | Miller |
| 2,436,853 A | 3/1948 | Coleman |
| 2,486,667 A | 11/1949 | Meister |
| 2,529,258 A | 11/1950 | Lobo |
| 2,543,284 A | 2/1951 | Gleason |
| 2,588,192 A * | 3/1952 | Akerman et al. .............. 601/44 |
| 2,762,366 A * | 9/1956 | Huxley, III et al. .......... 601/44 |
| 2,772,673 A | 12/1956 | Huxley, III et al. |
| 2,779,329 A | 1/1957 | Huxley, III et al. |
| 2,780,222 A | 2/1957 | Polzin et al. |
| 2,818,853 A | 1/1958 | Huxley, III et al. |
| 2,832,335 A | 4/1958 | Huxley, III et al. |
| 2,869,537 A | 1/1959 | Chu |

(Continued)

Primary Examiner—Danton DeMille
(74) Attorney, Agent, or Firm—Barnes & Thornburg

(57) ABSTRACT

A pneumatic chest compression vest is disclosed for the purposes of clearing the lungs of mucus and producing quality sputum samples for analysis. The vest is comprised of a first portion that has an air bladder mounted on its inner surface that applies a compressive force to the region of the chest that encompasses the lungs. The vest is removably adjustable and extends around a patient to hold the vest in the correct position for fitting and during treatment.

35 Claims, 8 Drawing Sheets

U.S. PATENT DOCUMENTS

| | | | | |
|---|---|---|---|---|
| 2,899,955 A | * | 8/1959 | Huxley, III et al. | 601/44 |
| 3,043,292 A | | 7/1962 | Mendelson | |
| 3,063,444 A | | 11/1962 | Jobst | |
| 3,120,228 A | | 2/1964 | Huxley, III | |
| 3,266,070 A | | 8/1966 | O'Link | |
| 3,310,050 A | | 3/1967 | Goldfarb | |
| 3,333,581 A | | 8/1967 | Robinson et al. | |
| 3,481,327 A | | 12/1969 | Drennen et al. | |
| 3,566,862 A | | 3/1971 | Schuh et al. | |
| 3,577,977 A | | 5/1971 | Ritzinger, Jr. et al. | |
| 3,683,655 A | | 8/1972 | White et al. | |
| 3,945,041 A | | 3/1976 | Rhee | |
| 3,993,053 A | | 11/1976 | Grossan | |
| 4,344,620 A | | 8/1982 | Debski | |
| 4,349,015 A | | 9/1982 | Alferness | |
| 4,397,306 A | | 8/1983 | Weisfeldt et al. | |
| 4,424,806 A | | 1/1984 | Newman et al. | |
| 4,453,538 A | | 6/1984 | Whitney | |
| 4,483,336 A | | 11/1984 | Deitch | |
| 4,561,853 A | | 12/1985 | Faulconer et al. | |
| 4,577,626 A | | 3/1986 | Marukawa et al. | |
| 4,621,621 A | | 11/1986 | Marsalis | |
| 4,637,074 A | | 1/1987 | Taheri | |
| 4,646,366 A | | 3/1987 | Nishida et al. | |
| 4,676,232 A | | 6/1987 | Olsson et al. | |
| 4,815,452 A | | 3/1989 | Hayek | |
| 4,838,263 A | | 6/1989 | Warwick et al. | |
| 4,840,167 A | | 6/1989 | Olsson et al. | |
| 4,928,674 A | | 5/1990 | Halperin et al. | |
| 4,930,498 A | | 6/1990 | Hayek | |
| 4,971,042 A | | 11/1990 | Lerman | |
| 4,977,889 A | | 12/1990 | Budd | |
| 5,056,505 A | * | 10/1991 | Warwick et al. | 601/44 |
| 5,076,259 A | | 12/1991 | Hayek | |
| 5,101,808 A | | 4/1992 | Kobayashi et al. | |
| 5,188,097 A | | 2/1993 | Hansen | |
| 5,222,478 A | | 6/1993 | Scarberry et al. | |
| 5,261,394 A | | 11/1993 | Mulligan et al. | |
| 5,277,194 A | | 1/1994 | Hosterman et al. | |
| 5,299,599 A | | 4/1994 | Farmer et al. | |
| 5,453,081 A | | 9/1995 | Hansen | |
| 5,455,159 A | | 10/1995 | Mulshine et al. | |
| 5,496,262 A | | 3/1996 | Johnson, Jr. et al. | |
| 5,548,843 A | * | 8/1996 | Chase et al. | 602/19 |
| 5,562,604 A | | 10/1996 | Yablon et al. | |
| 5,569,170 A | | 10/1996 | Hansen | |
| 5,769,797 A | | 6/1998 | Van Brunt et al. | |
| 5,769,800 A | * | 6/1998 | Gelfand et al. | 601/151 |
| 5,806,512 A | | 9/1998 | Abramov et al. | |
| 5,891,062 A | | 4/1999 | Schock et al. | |
| 5,997,488 A | | 12/1999 | Gelfand et al. | |
| 6,030,353 A | | 2/2000 | Van Brunt | |
| 6,155,996 A | | 12/2000 | Van Brunt et al. | |
| 6,210,345 B1 | | 4/2001 | Van Brunt | |
| 6,340,025 B1 | | 1/2002 | Van Brunt | |
| 6,379,316 B1 | | 4/2002 | Van Brunt et al. | |
| 6,415,791 B1 | | 7/2002 | Van Brunt | |
| 6,471,663 B1 | | 10/2002 | Van Brunt et al. | |
| 2002/0082531 A1 | | 6/2002 | Van Brunt et al. | |

* cited by examiner

PNEUMATIC CHEST COMPRESSION VEST WITH FRONT PANEL AIR BLADDER

CROSS-REFERENCE TO RELATED APPLICATION(S)

This application is a continuation-in-part of U.S. patent applications Ser. No. 09/387,319 now abandoned, "Pneumatic Chest Compression Vest with Front Panel Bib;" Ser. No. 09/387,339, "Chest Compression Vest with Connecting Belt," issued as U.S. Pat. No. 6,471,663; and Ser. No. 09/387,312, "Method and Apparatus for Inducing Sputum Samples for Diagnostic Evaluation," issued as U.S. Pat. No. 6,379,316; which all were filed on Aug. 31, 1999 and which are all assigned to the same assignee as the present application.

BACKGROUND OF THE INVENTION

The present invention relates to chest compression devices and in particular to a high frequency chest wall oscillator device.

Manual percussion techniques of chest physiotherapy have been used for a variety of diseases such as cystic fibrosis, emphysema, asthma, and chronic bronchitis, to remove the excess mucus that collects in the lungs. To bypass dependency on a caregiver to provide this therapy, chest compression devices have been developed to produce high frequency chest wall oscillation (HFCWO), the most successful method of airway clearance. In addition, these devices can be utilized for diagnosis and treatment of pulmonary disorders such as lung cancer, asthma, chronic obstructive pulmonary disease (COPD), tuberculosis, *Pneumocystis carinii* pneumonia (PCP), inflammation, and infection.

The device most widely used to produce HFCWO is The Vest™ airway clearance by the assignee of the present application. A description of the pneumatically driven system can be found in the Van Brunt et al. patent, U.S. Pat. No. 5,769,797, which is assigned to the same assignee as the present application. Another pneumatic chest compression device has been described by Warwick et al., U.S. Pat. No. 4,838,263.

Pneumatically driven HFCWO produces substantial transient increases in the airflow velocity with a small displacement of the chest cavity volume. This action produces a cough-like shear force and reduction in mucus viscosity that results in an upward motion of the mucus.

BRIEF SUMMARY OF THE INVENTION

The present invention is a pneumatic chest compression vest that loosens and helps remove mucus from a person's lungs or induces production of sputum samples for further diagnostic analysis. The vest is designed to focus the compressive force on the region of the chest that encompasses the lungs.

One aspect provides a pneumatic chest compression vest including a first portion having an outer surface and an inner surface, the first portion adapted to be positioned over a first part of a circumference of a torso of a patient, the first portion being substantially non-stretchable, a second portion adapted to be positioned over a second part of the circumference of the torso of the patient, the second portion substantially non-stretchable and non-inflatable, the first portion and second portion removably circumscribing the torso of the patient, an air bladder mounted on the inner surface of the first portion, the air bladder having at least one opening through which the air bladder is connectable to a source of oscillating pneumatic pressure, and wherein the air bladder is adapted to be positioned over a portion of the circumference of the torso of the patient.

Another aspect provides a pneumatic chest compression vest including a first portion and a second portion, the first portion and the second portion adapted to removably circumscribe a torso of a patient, the first portion and the second portion being substantially non-stretchable, an air bladder mounted on an inner surface of the first portion, the air bladder having at least one opening through which the air bladder is connectable to a source of oscillating pneumatic pressure, and a fitting and fastening system. The fitting and fastening system may include a plurality of adjustable fasteners adapted to adjust and fasten the vest about the torso of the patient, at least one handgrip attached to the vest, the handgrip adapted to ease placement of the adjustable fasteners, and a plurality of stiffeners attached to the vest, the stiffeners adapted to position the handgrip about the torso of the patient.

Another aspect provides a pneumatic chest compression vest including a first portion and a second portion adapted to be positioned about a circumference of a torso of a patient and first means for positioning, fitting, and removably fastening the first portion and the second portion about the torso of the patient.

Another aspect provides a pneumatic chest compression vest including a first portion and a second portion adapted to be positioned about a circumference of a torso of a patient, and second means for applying an oscillating pressure to lungs of a patient, the second means attached to the first portion and only partially circumscribing a torso of the patient.

DETAILED DESCRIPTION

Figure 1:
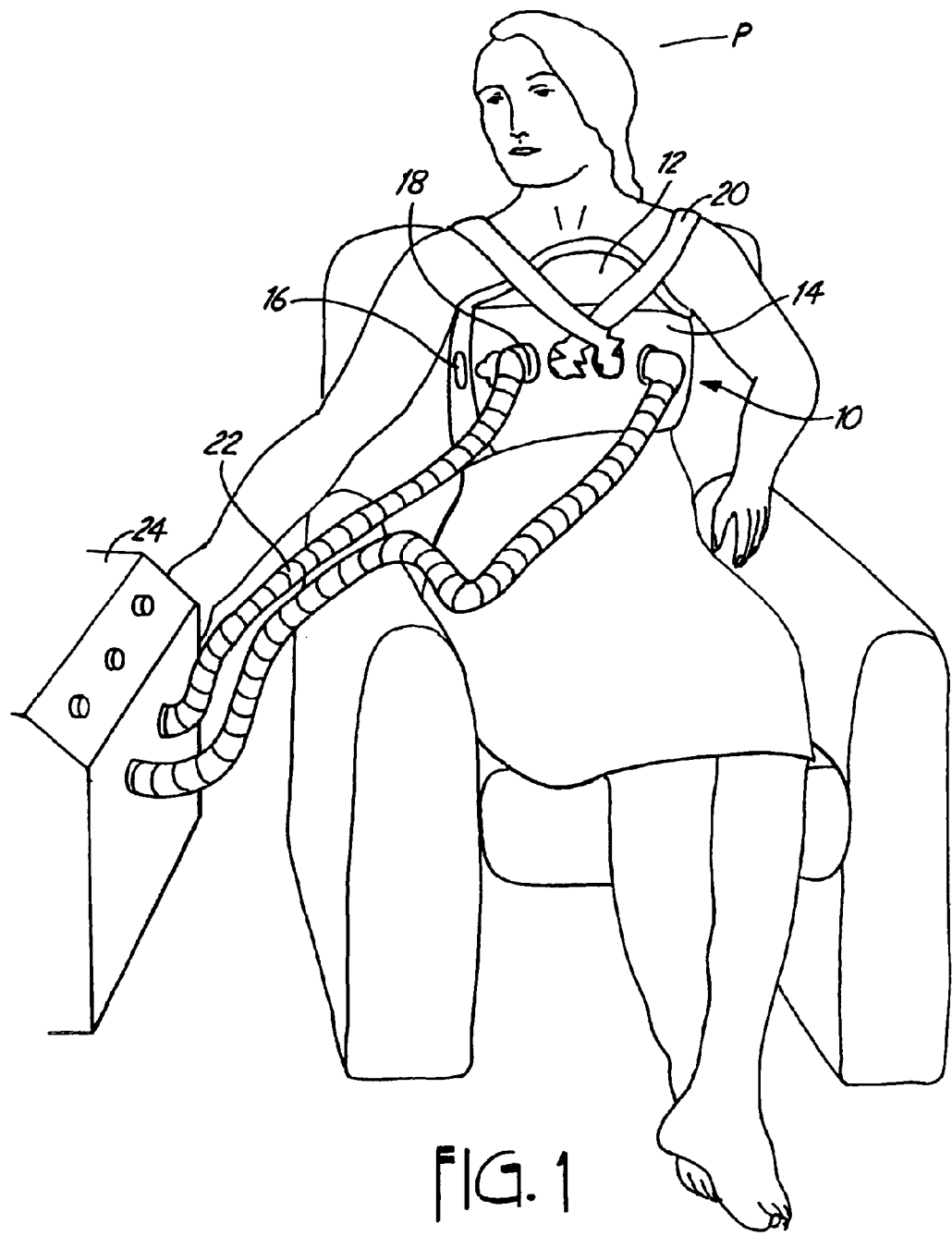
FIG. 1 shows a person wearing one embodiment of a pneumatic chest compression vest.

FIG. 1 shows pneumatic chest compression vest 10 of one embodiment of the present invention fitted onto patient P. Pneumatic chest compression vest 10 is shown with front panel 12, belt 14 with belt holes 16, air couplings 18, suspenders 20, hoses 22, and pneumatic pressure generator 24. Front panel 12 of pneumatic chest compression vest 10 covers from approximately the bottom of the patient's rib cage to near the patient's collar bone and extends over the front of the patient's chest to under the patient's arms. Belt 14, which is attached to one side of front panel 12, wraps around the patient's back and across front panel 12. Pneumatic chest compression vest 10 is secured by aligning belt holes 16 with air ports (not shown) on front panel 12 so that air couplings 18 can insert through belt holes 16 and the air ports. Suspenders 20 are also attached to secure pneumatic chest compression vest 10 in place. One end of hoses 22 attaches to air couplings 18 and the other end attaches to pneumatic pressure generator 24. Pneumatic pressure generator 24 provides the oscillating pressure to vest 10 to apply compressive force to the patient's chest. Pneumatic chest compression vest 10 and its operation will be described in more detail in subsequent figures.

Figure 2:
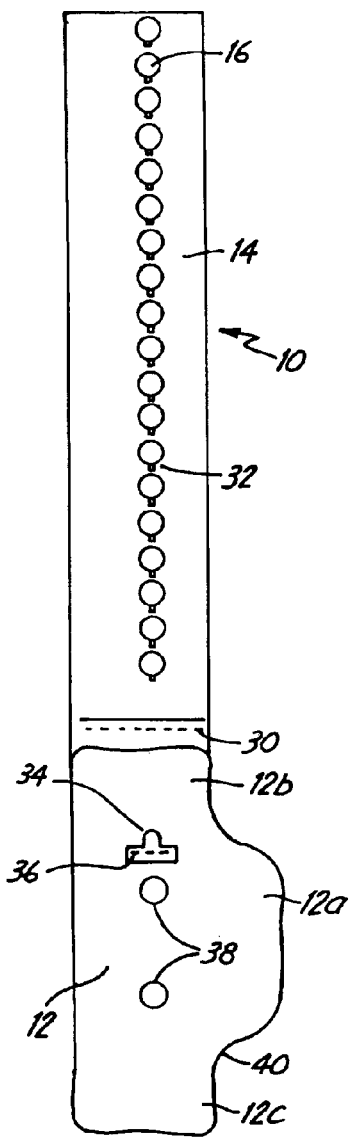
FIG. 2 is a front view of one embodiment of a pneumatic chest compression vest.

FIG. 2 is a front view of pneumatic chest compression vest 10 laid flat. Front panel 12 is comprised of central bib portion 12a, side portions 12b and 12c, tab 34, tab seams 36, air ports 38, and liner seam 40. Belt 14, which attaches to front panel 12 at belt seam 30, contains belt holes 16 with slits 32.

Pneumatic chest compression vest 10 wraps around the torso of patient P. Belt 14 of pneumatic chest compression vest 10 extends around the back of patient P and across the outer surface of front panel 12. Belt 14 contains longitudinally positioned belt holes 16 each of which includes a slit 32. Tab 34 is welded onto front panel 12 at tab seams 36 and inserts into one of the belt holes 16.

Pneumatic chest compression vest 10 is secured in place by overlapping belt holes 16 with air ports 38 on front panel 12. The distance between air ports 38 corresponds to a multiple of the distance between each belt hole 16. In one embodiment, the diameter of belt holes 16 and air ports 38 is about 1.4 inches with belt holes 16 centered about 2 inches apart, and air ports 38 are centered about 6 inches apart. Tab 34 is welded to front panel 12 at tab seams 36 so that it aligns with air ports 38 on front panel 12 in such a way that as belt 14 wraps around patient P and extends across the outer surface of front panel 12, tab 34 can insert into a belt hole 16. When tab 34 is inserted into a belt hole 16, corresponding belt holes 16 will align with air ports 38. Once aligned, air couplings 18 can easily be snapped into belt holes 16 and air ports 38 (See FIG. 1). Depending on the circumference of the patient's torso, different belt holes 16 will align with tab 34 and air ports 38. This allows adjustment of pneumatic chest compression vest 10 so that it fits securely around patient P.

Slits 32 may be about 0.2 inch long. Slits 32 allow ease of insertion of suspenders 20 into belt holes 16 (See FIG. 1).

Liner seam 40 extends along the perimeter of front panel 12 encompassing central bib portion 12a, which may have a height of about 11.75 inches but can be from about 9.0 to about 13.0 inches, and side portions 12b and 12c, which may have a height of about 7.75 inches but can be from about 6.0 to about 9.0 inches.

Figure 3:
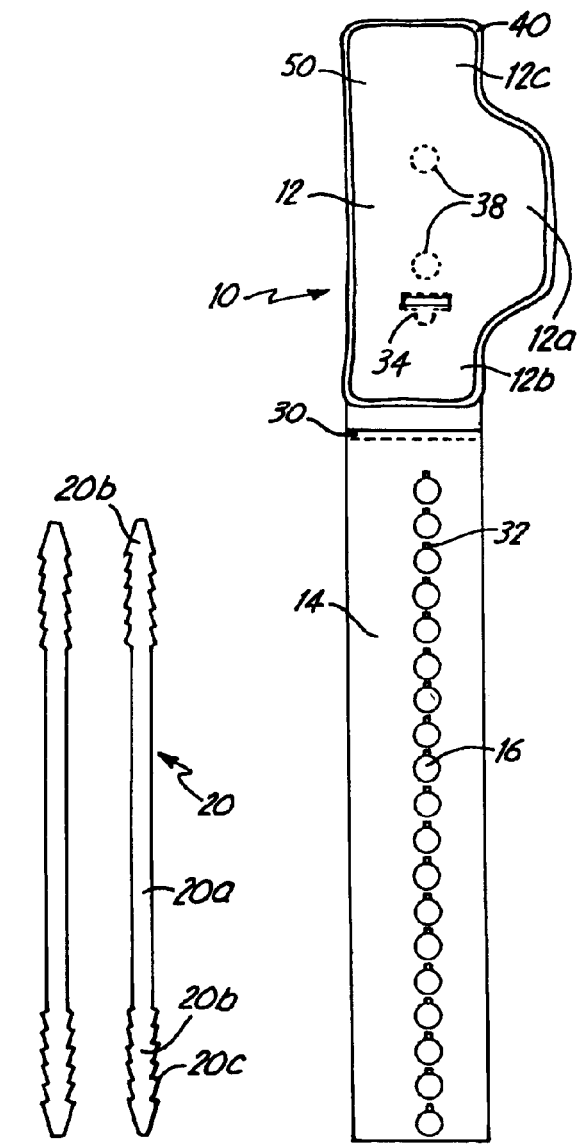
FIG. 3 is a back view of one embodiment of a pneumatic chest compression vest.

FIG. 3 is a back view of pneumatic chest compression vest 10 laid flat. Front panel 12 includes central bib portion 12a, side portions 12b and 12c, air ports 38 (in phantom), and liner seam 40. A liner 50 is shown welded to the inner surface of front panel 12 along liner seam 40. Belt 14, belt holes 16 with slits 32, belt seam 30, and tab 34 (in phantom) are shown and were described in FIG. 2.

Liner 50 may be made of an elastic material such as 4 mil polyethylene, and the remaining parts, except air couplings 18, are made of an inelastic material such as 8 mil polycarbonate or 20 mil polyethylene. These materials are relatively inexpensive and can be easily incinerated, producing no toxic emissions and little particulate matter for disposal. Liner 50 mounted onto front panel 12 defines an air bladder that is about 21 inches wide.

In operation, the air bladder is inflated via air ports 38 against the chest of patient P to apply a compressive force to the patient's lungs. Side portions 12b and 12c allow the air bladder to extend under the arms of patient P. Thus, the air bladder also compresses the sides of the torso that cover the patient's lungs. The combination of a generally rigid outer surface and flexible bladder prevents the vest from taking on a circular shape when the air bladder is inflated. Instead, inflating the air bladder forces the chest to change shape so that most of the motion during compression is inward, and the outward force is minimized. This increases the efficiency of the system. The volume of the air bladder is also reduced over the prior art vests, which makes the system more efficient in terms of applying the sane volume of air over a smaller surface area so that the magnitude of force necessary for deep sputum induction is achieved.

Pneumatic chest compression vest 10 is suitable for typical pressure requirements of about 0.5 to about 1.0 P.S.I., and can operate for about 30 to about 45 minutes during an oscillatory chest compression treatment. It may last longer for other less stringent applications.

Figure 4:
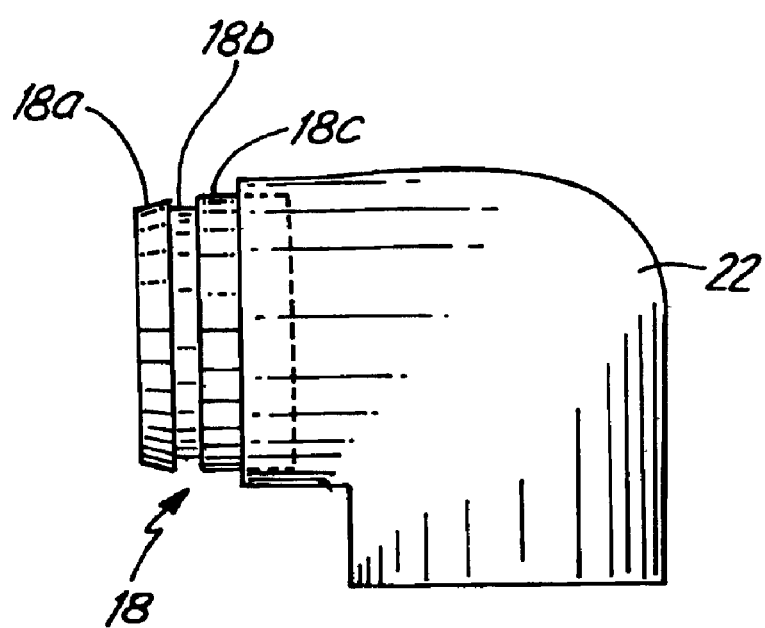
FIG. 4 is a side view of one embodiment of an air coupling connected to a hose.

FIG. 4 shows a side view of air coupling 18 connected to hose 22. Air coupling 18 includes head 18a, neck 18b, and body 18c (shown partially in phantom). A portion of hose 22 is shown partially enclosing body 18c of air coupling 18.

In one embodiment, air coupling 18 is made of aluminum with a height of about 3.25 inches. The height of head 18a is about 0.85 inches, neck 18b is about 0.75 inches, and body 18c is about 1.65 inches and is removably attached to neck 18b. Also, hose 22 is angled about 90 degrees at the end that connects to air coupling 18.

Head 18a is beveled with the diameter increasing from about 1.30 inches to about 1.40 inches. The inside diameter of head 18a is about 1.15 inches. Neck 18b has a diameter of about 1.36 inches. Body 18c has a diameter of about 1.50 inches with an inside diameter of about 1.20 inches. The inside diameter of air coupling 18 increases from head 18a to body 18c.

The operation of air coupling 18 is discussed in reference to other parts of pneumatic chest compression vest 10 that are not shown. Head 18a snaps through belt holes 16 and air ports 38 into the air bladder. Neck 18b remains within front panel 12 and belt 14 to secure pneumatic chest compression vest 10 around patient P. Hose 22 connects to and partially overlaps body 18c, which is not connected to neck 18b at this point. Body 18c, when connected to neck 18b, remains on the external side of pneumatic chest compression vest 10. Thus, air coupling 18 has dual functions-to secure pneumatic chest compression vest 10 and provide a coupling to attach hose 22. With hose 22 essentially hanging parallel to front panel 12, hose 22 hangs in a manner which keeps air coupling 18 from pulling outward on pneumatic chest compression vest 10.

Figure 5:
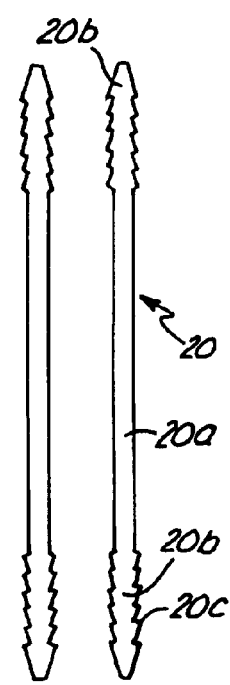
FIG. 5 is a top view of one embodiment of a suspender.

FIG. 5 shows suspender 20 laid flat. Suspender 20 is comprised of strap 20a and serrated ends 20b that include serrations 20c.

In one embodiment, the length of suspender 20 is about 35.0 inches. Serrated ends 20b are about 7 inches long, and each includes about 6 approximately 1 inch long serrations 20c. Strap 20a has a width of about 1.1 inches. Serrations 20c extend out to about 1.6 inches.

In operation, suspenders 20 extend from the front to the back of pneumatic chest compression vest 10 and insert into two of the belt holes 16 on the front and another pair of belt holes 16 in the back. Serrations 20c allow suspenders 20 to be adjusted to the proper length for a secure fit. In one embodiment, suspenders 20 are crossed in front of patient P to minimize movement or slippage of pneumatic chest compression vest 10 during treatment (See FIG. 1).

Figure 6:
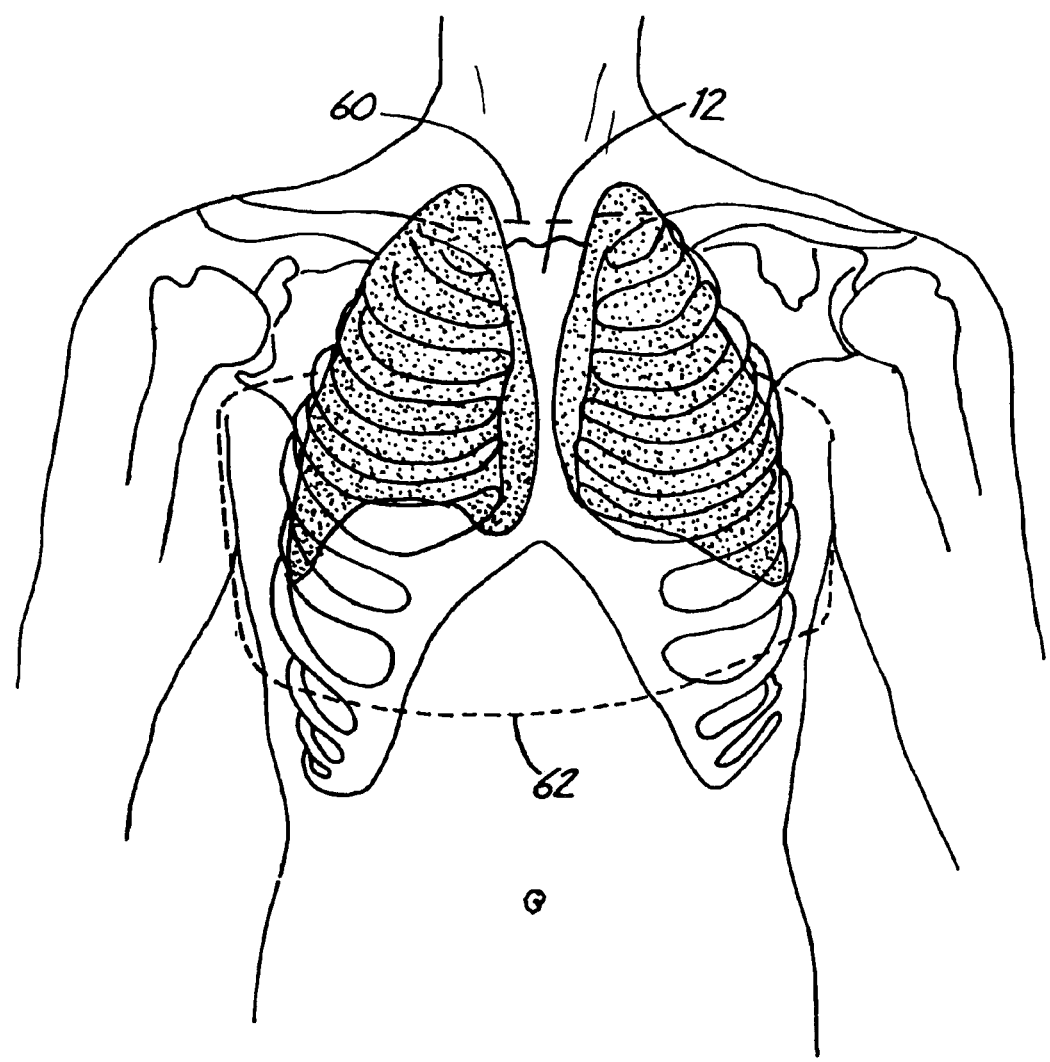
FIG. 6 shows where a person's lungs are located relative to the pneumatic chest compression vest.

FIG. 6 illustrates how pneumatic chest compression vest 10 is positioned with respect to the patient's lungs and skeletal structure. An outline of front panel 12 with top edge 60 and bottom edge 62 of pneumatic chest compression vest 10 indicates the region of the patient's chest that is covered.

In operation, front panel 12 preferably covers the region of the torso that encases the lungs of patient P. Top edge 60 is positioned near the patient's collarbone, and bottom edge 62 is positioned near the bottom of the patient's rib cage. Compression on the abdomen is minimized, and top edge 60 reaches up to the upper lobes of the lungs to facilitate mucus removal in the upper lobes. Thus, the improved design increases the efficiency of the system to obtain sufficient sputum induction and mucus mobilization.

Figure 7:
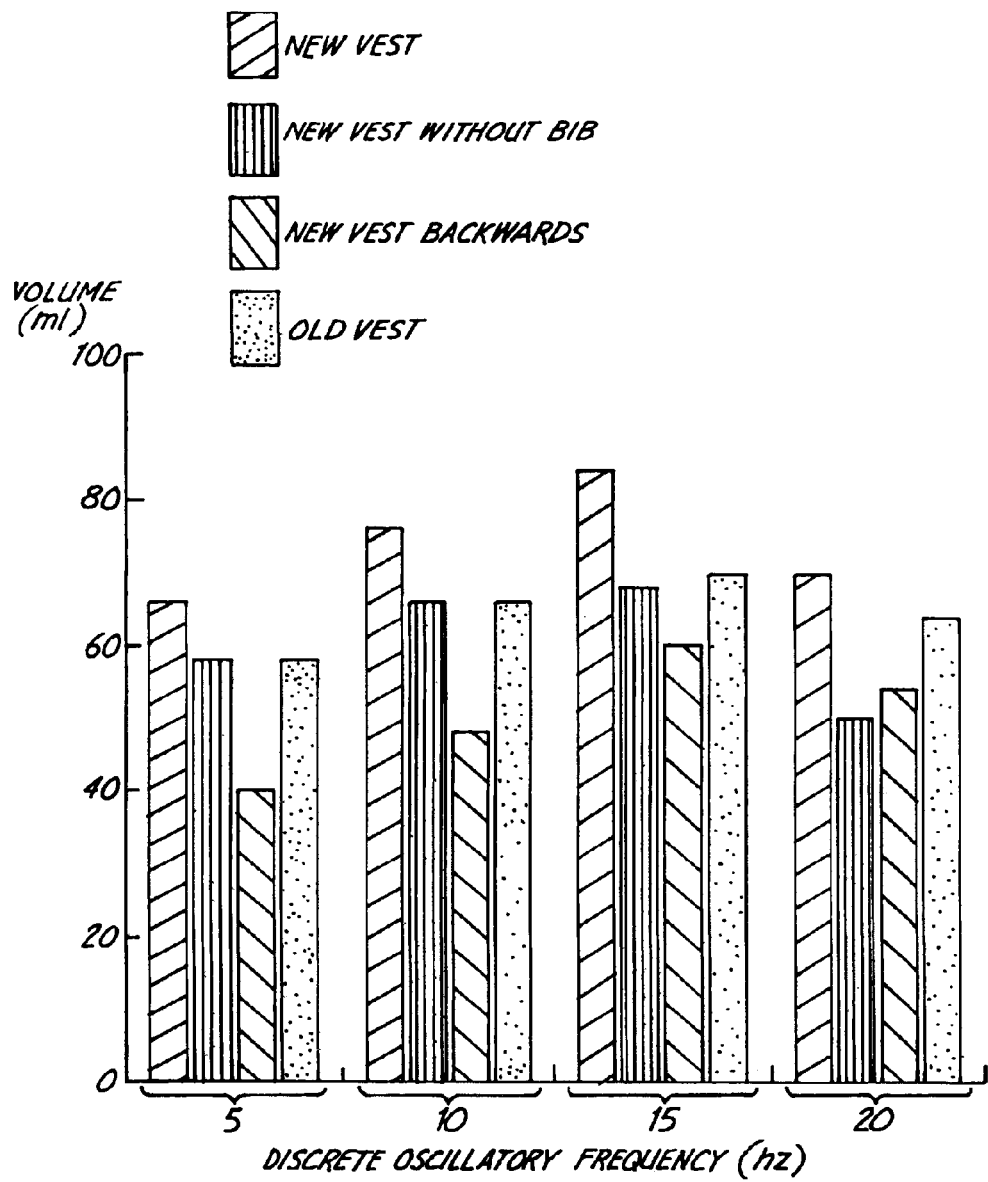
FIG. 7 is a graph illustrating the performance of one embodiment of a pneumatic chest compression vest.

FIG. 7 shows the results of a comparison done between one embodiment (new vest), an embodiment without the bib section of central bib portion 12a (new vest w/o bib), an embodiment positioned backwards (new vest backwards), and a prior art vest (old vest). FIGS. 2 and 3 provide a view of the bib section of central bib portion 12a. The bib section is the part of front panel 12 that compresses the upper lobes of the lungs. Peak expiratory volume (peak volume) was measured on a single subject with each variation over an oscillatory frequency range between 5 and 20 Hertz. The subject was fitted with a vest and given a mouthpiece with a hose attached to a volume chamber. The volume chamber was equipped with a sensor that measured changes in oscillatory volume. Expiratory volumes were measured with each vest variation tested at 5, 10, 15, and 20 Hertz. The graph illustrates that one embodiment with the front panel over the patient's chest and the bib portion extending to about the collarbone produces higher peak volume of airflow. The high peak volume of airflow corresponds to an increased force asserted on the mucus that results in increased mobilization.

Figure 8:
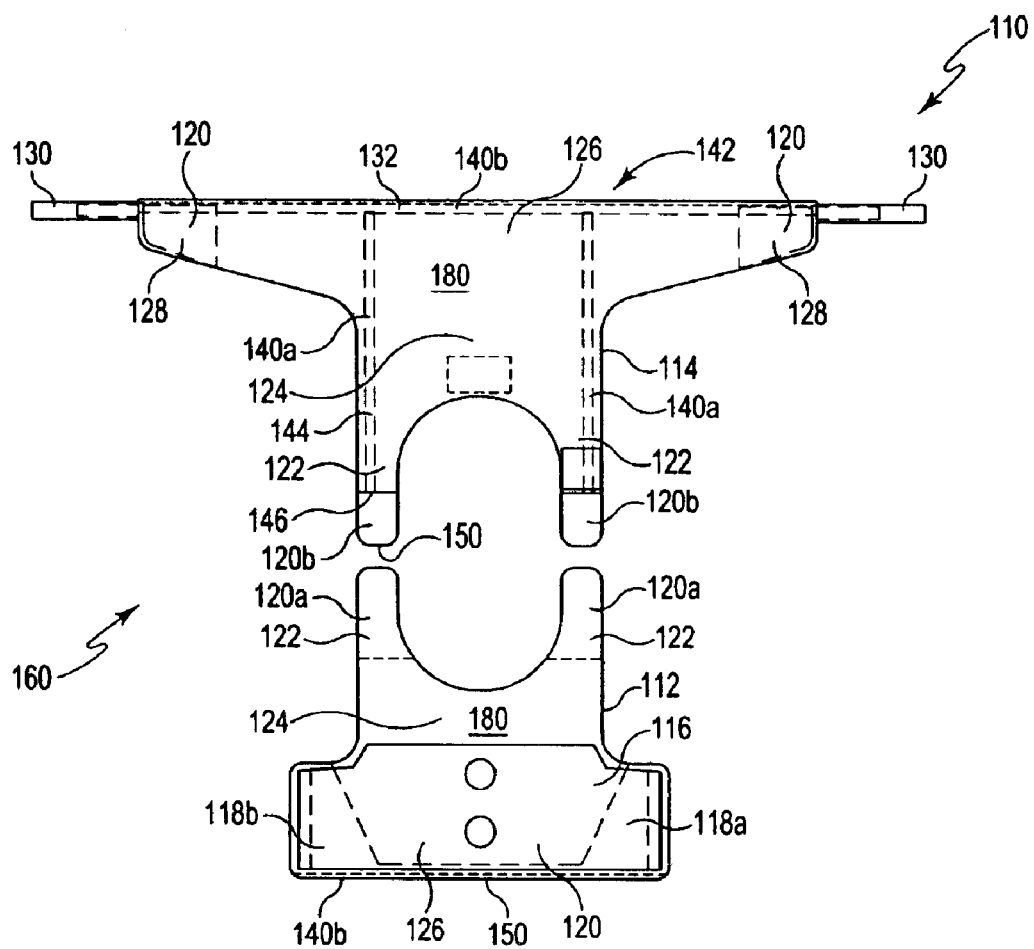
FIG. 8 is a top view of a second embodiment of a pneumatic chest compression vest.

FIG. 8 shows a second embodiment of a pneumatic chest compression vest 110. Vest 110 has a first portion 112 and a second portion 114. The first portion 112 and the second portion 114 each have an inner surface 180 and an outer surface (reverse side not shown). The first portion 112 has an air bladder 116. The air bladder 116 may be formed as a separate part as shown, or may be integral with the first portion 112. (See FIG. 9). The first portion 112 and second portion 114 are made of a flexible non-stretchable material, such as a polyester material, such as Hydra-tuff 600 denier polyester with a 7 ounce per square yard PVC laminate. The material is substantially non-stretchable so that the first portion and the second portion remain substantially unchanged in general shape when subjected to a source of oscillating pneumatic pressure.

The first portion 112 and air bladder 116 are adapted to be positioned in front of a person's torso, however, the first portion 112 may also be positioned in back of the torso. The first portion 112 has two bladder pockets 118a, 118b for securing the air bladder to the inner surface 180 of the first portion. Optionally, a single bladder pocket, or additional bladder pockets may be used to secure the air bladder to the first portion.

The vest 110 includes a fitting and fastening system 160 for custom fitting of the vest to the patient and for ease in fastening the vest about a person's torso. The first portion 112 and second portion 114 each are adapted to partially circumscribe the torso of a patient. The air bladder is adapted to be positioned over a portion of the torso, such as the front, the front and sides, the back, the back and sides, or less than 75% of the circumference of the torso.

The fitting and fastening system 160 includes a two-part vest 112, 114, hook and loop fasteners 120, handgrips 130, and stiffeners 140. The two part vest comprises a first portion 112 and a second portion 114. The first portion 112 is adapted to be positioned on the front of a person's torso and the second portion is adapted to be positioned on the back of a person's torso. The first and second portions each have two shoulder straps 122, a mid portion 124 (to allow room for the arms) and a bottom portion 126.

Hook and loop fasteners 120 are located on the shoulder straps 126 with the loop fasteners 120a on the first portion 112 and the hook fasteners 120b on the second portion 114. Optionally, the hook 120b and loop 120a fasteners could be reversed or other fasteners could be used to secure the shoulder straps 122 in position. The loop portion 120a of the fastener extends the length of the shoulder strap 122 allowing adjustment of the length of the shoulder straps.

Hook and loop fasteners 120 are located on the bottom portion 126 of the first portion 112 and the bottom portion 126 of the second portion 114. The bottom portions 126 of the first and second portions are adapted to fasten together with hook and loop fasteners to circumscribe the torso of the patient. Loop fasteners are positioned on the ends 128 of the second portion 114 and hook fasteners are located on the front (hidden side) of the bottom portion 126 of the first portion 112. Optionally, the hook and loop portions could be reversed or other fasteners could be used to secure the first and second portions in position. Hook and loop fastening material extends over substantially the entire bottom portion of the first portion allowing adjustment of the circumference of the vest.

Handgrips 130 are positioned at the end 128 of the bottom portions 126 of the second portion 114. The handgrips 130 provide for easier fitting and securing of the vest. The handgrips 130 extend from the edge 128 of the of the bottom portion. The handgrips 130 are comprised of flexible material such as one inch looped polypropylene strapping material. The handgrips 130 extend parallel to the bottom edge 132 of the second portion, or optionally at an angle upwardly or downwardly from parallel.

Stiffeners 140 are attached to the vest at various positions to provide a stiffener system 142. The stiffener system 142 includes vertical stiffeners 140a and horizontal stiffeners 140b. Optionally, vertical or horizontal stiffeners may be used or other positions, such as diagonal may be used, either separately, or in combination. The stiffeners 140 allow the vest to be at least temporarily formed by hand to a particular shape. The stiffeners 140 are comprised of a rigid formable material, such as metal, such as 16 Gauge insulated copper wire. Optionally, other rigid formable materials, such as plastic may be used. The stiffeners 140 may be permanently attached to the vest, such as by sewing into the hem, such as along the bottom edge 132 of the vest, or optionally, the stiffeners can be removably attached to the vest by locating the stiffener 140 in a pocket 144 with an opening 146 through which the stiffener may be removed. The stiffeners provide at least temporary rigidity to portions of the vest. The rigidity of the vest allows the vest to be more easily positioned about the torso for fastening. For example, stiffeners are positioned in the shoulder straps 122 so that the first portion and second portion may be positioned on the shoulders. Secondly, the stiffeners 140 are positioned along the bottom edge 132 of the second portion so that the bottom portion may be formed around the torso. Thirdly, the stiffeners are positioned so that the handgrips 130 are positioned for easier reach, such as at the sides or in front of the torso.

The embodiment shown in FIG. 8 has two vertical stiffeners in the second portion 114, each extending from about 1 inch from the end 150 of the shoulder straps along the length of the shoulder straps to the bottom edge 132 of the second portion. The embodiment also has two vertical stiffeners in the first portion extending along the outside edge of the bottom portion. The embodiment has two horizontal stiffeners, a horizontal stiffener 140b along the bottom edge 150 of the first portion 112 and second horizontal stiffener along the bottom edge 132 of the second portion 114.

Figure 9:
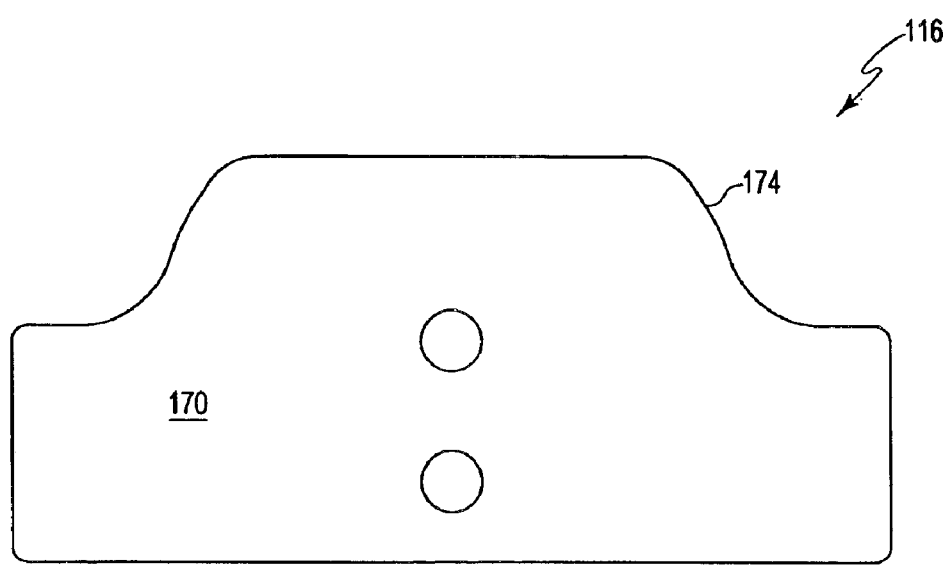
FIG. 9 is a top view of one embodiment of a removable air bladder.

FIG. 9 shows one embodiment of an air bladder 116. The bladder 116 has a front panel 170 and a back panel 172 (hidden) sewn together at the outside edge 174. The front panel and back panel are a flexible, non-stretchable airtight material such as 600 denier polyester with 7 ounces per square yard PVC laminate. However, other substantially airtight inflatable materials, such as rubber may also be used. The front panel has two openings for two connectors, similar to those shown in FIG. 4.

The bladder may be sized and shaped such that the bladder 116 covers substantially the entire front lung area as shown in FIG. 6. The bladder 116 may be sized and shaped such that the bladder covers the bottom portion 126 and the mid portion 124 of the first portion 112 (See FIG. 8). Optionally, the bladder 116 covers only the bottom portion 126.

Figure 10:
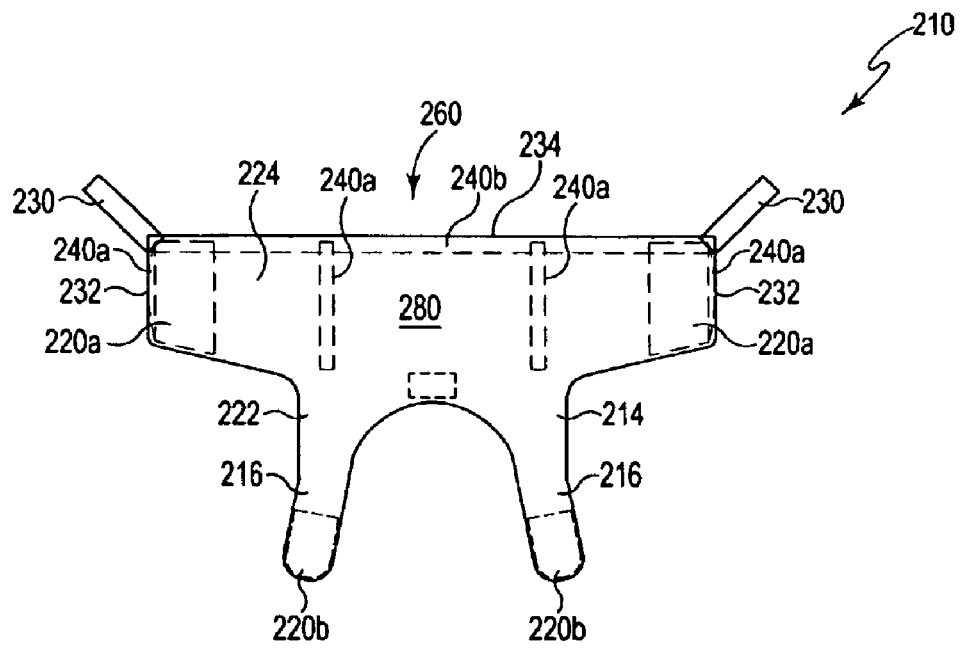
FIG. 10 is a top view of a third embodiment of a pneumatic chest compression vest.
Figure 10:
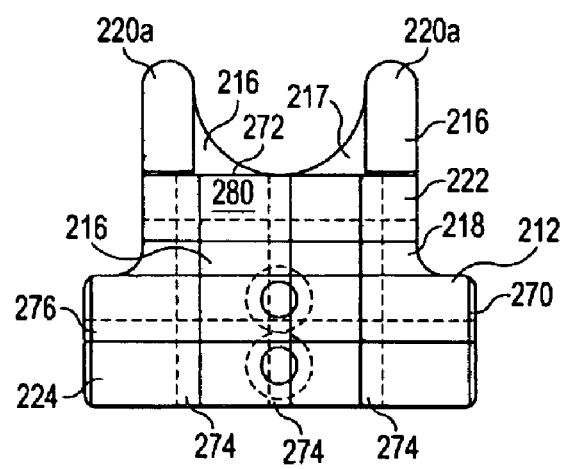

FIG. 10 shows a third embodiment of a pneumatic chest compression vest 210. Vest 210 has a first portion 212 and a second portion 214. The first portion 212 and the second portion 214 each have an inner surface 280 and an outer surface (Reverse side not shown). The first portion 212 has an air bladder 216. The air bladder 216 may be integral with the first portion, as shown, or formed out of separate panels as previously shown in FIG. 8. The first portion and second portion are made of a flexible material, such as a polyester material with a PVC laminate, such as Hydra-tuff 600 denier polyester with a 7 ounce per square yard PVC laminate. The material is substantially non-stretchable so that the first portion and the second portion remain substantially unchanged in shape when subjected to a source of oscillating pneumatic pressure.

The first portion 212 including the air bladder 216 are adapted to be positioned in front of a person's torso, however, the first portion may also be positioned in back of the torso. The first portion has an integral bladder 216 formed to it by securing a second panel 218 to a portion of one side 217 of the first portion 212 forming an inner surface 280. The second panel 218 is comprised of a flexible airtight material, such as PVC coated polyester material. The second panel 218 is secured to the first portion 212 in a pleated arrangement so that the air bladder 216 can expand to a larger volume. The first portion 212 and the second portion 214 each are adapted to partially circumscribe the torso of a patient. The air bladder is adapted to be positioned over a portion of the torso, such as the front, front and sides, back, back and sides, or less than about 75% of the circumference of the torso.

The vest 210, like the previous embodiment also includes a fitting and fastening system 260 for custom fitting of the vest to the patient and for ease in fastening the vest about a person's torso. The first portion and second portion are adapted to removably circumscribe the torso.

The fitting and fastening system includes a two-part vest 212, 214, hook and loop fasteners 220, handgrips 230, and stiffeners 240. The two-part vest comprises a first portion 212 and a second portion 214. The first portion 212 is adapted to be positioned on the front of a person's torso and the second portion 214 is adapted to be positioned on the back of a person's torso. The first and second portions each have two shoulder straps 216, a mid portion 222 (to allow room for the arms) and a bottom portion 224. The shoulder straps 216 of the second portion 214 are angled outwardly to allow easier attachment and better fit of the shoulder straps to the first portion.

Hook and loop fasteners 220 are located on the shoulder straps 216 with the loop 220a on the first portion 212 and the hook fasteners 220b on the second portion 214. Optionally, the hook and loop portions could be reversed or other fasteners could be used to secure the shoulder straps in position. The loop portion 220a of the fastener extends substantially the length of the shoulder strap 216 allowing adjustment of the length of the shoulder straps.

Hook and loop fasteners 220 are located on the bottom portion 224 of the first portion 212 (on the reverse side) and the bottom portion 224 of the second portion 214. The bottom portions 224 of the first and second portions are adapted to fasten together with hook and loop fasteners to circumscribe the torso of the patient. Loop fasteners 220a are positioned on the ends of the second portion 214 and hook fasteners are located on the front (reverse side) of the first portion 212. Optionally, the hook and loop portions could be reversed or other fasteners could be used to secure the first and second portions in position. Hook and loop fastening material extends over substantially the entire bottom portion 212 of the first portion allowing adjustment of the circumference of the vest.

Handgrips 230 are positioned at the edge 232 of the bottom portions of the second portion. The handgrips 230 provide for easier fitting and securing of the vest. The handgrips 230 extend from the edge 232 of the of the bottom portion. The handgrips 230 are comprised of flexible material such as one inch looped polypropylene strapping material. The handgrips 230 extend downwardly from parallel of the bottom edge 234 of the second portion, or optionally at an angle upwardly or extending substantially parallel.

Stiffeners 240 are attached to the vest at various positions to provide a stiffener system 260. The stiffener system 260 includes vertical stiffeners 240a and horizontal stiffeners 240b. Optionally, vertical or horizontal stiffeners may be used or other positions, such as diagonal may be used, either separately, or in combination. The stiffeners 240 allow the vest to be at least temporarily formed by hand to a particular shape. The stiffeners 240 are comprised of a rigid formable material, such as metal, such as 14 Gauge insulated copper wire. Optionally, other rigid formable materials, such as plastic may be used. The stiffeners 240 may be permanently attached to the vest, such as by sewing into the hem, such as along the bottom edge 234 or outside edges 232 of the vest, or optionally, the stiffeners can be removably attached to the vest by locating the stiffener in a pocket with an opening through which the stiffener may be removed. The stiffeners provide at least temporary rigidity to portions of the vest. The rigidity of the vest allows the vest to be more easily positioned about the torso for fastening. First, the stiffeners are positioned along the bottom edge of the second portion so that the bottom portion may be formed around the torso. Secondly, stiffeners are positioned along the outside edge 232 of the second portion and vertically in the middle of the second portion to provide rigidity for ease of fastening. Thirdly, the stiffeners are positioned so that the handgrips 230 are positioned for easier reach, such as at the sides or in front of the torso.

The embodiment shown in FIG. 10 has four vertical stiffeners in the second portion, two vertical stiffeners extending from about 1 inch from the base of the shoulder straps to the bottom edge of the second portion and two vertical stiffeners extending substantially along the outside edge of the bottom portion. The embodiment has one horizontal stiffener along the bottom edge of the second portion.

FIG. 10 shows an integral air bladder 216. Air bladder 216 is formed by a front panel 217 of the first portion and a second panel 218 sewn together at the outside edge 270 and horizontally approximately at the base 272 of the shoulder straps. The front panel 217 is a flexible, non-stretchable airtight material such as 600 denier polyester with 7 ounces per square yard PVC laminate. The second panel 218 is a flexible non-stretch airtight material such as 200 denier nylon material coated with 7 ounces per square yard PVC laminate. The second panel 218 is secured to the front panel 217 in a pleated pattern. The pleated pattern provides a larger more conforming air bladder. The material is overlapped approximately one inch every 6 inches creating approximately three horizontal pleats 274 and two vertical pleats 276. The front panel has two openings for two connectors, such as those shown in FIG. 4.

The bladder is sized and shaped such that the bladder covers substantially the entire front lung area as shown in FIG. 6. The bladder is sized and shaped such that the bladder covers the bottom portion and the mid portion of the front portion.

In operation, one embodiment of the present invention provides a method of providing high frequency chest wall oscillation to a patient, the method including fitting on a patient a vest having a first portion with an air bladder so that the air bladder is positioned in contact with a limited portion of a torso of a patient that encompasses lungs of the patient; and supplying an oscillating pneumatic pressure to the air bladder so that pressure is applied by the air bladder to the lungs. The method optionally includes positioning the vest with stiffeners, adjusting a circumference of the vest with adjustable fasteners, placing the vest over a head of the patient, securing the vest in position with adjustable fasteners with the adjustable fasteners positioned at a point away from a center of a chest of the patient, or securing the vest with shoulder straps which extend over shoulders of the patient.

Another embodiment provides a method of providing chest wall oscillation to a patient including positioning a vest on a patient so that an air bladder carried on an inner surface of a first portion of the vest is located adjacent a chest of the patient and applying pneumatic pressure through the air bladder over an area on the chest of the patient from about a bottom of a rib cage to a collarbone.

Another embodiment provides a method of providing chest wall oscillation to a patient including positioning a vest carrying an air bladder so that the air bladder engages only a portion of a torso of a patient and applying pressure through the air bladder to the torso of the patient.

Another embodiment provides a method of providing high frequency chest wall oscillation to a patient including mounting on a patient a vest having a first portion with an air bladder so that the air bladder is positioned in contact with a region of a chest of a patient that encompasses lungs of the patient and supplying an oscillating pneumatic pressure to the air bladder so that pressure is applied by the air bladder to the lungs of the patient.

Although the present invention has been described with reference to preferred embodiments, workers skilled in the art will recognize that changes may be made in form and detail without departing from the spirit and scope of the invention.

What is claimed is:

1. A pneumatic chest compression vest comprising:
    a first portion adapted to be positioned in front of a patient's torso, the first portion having an air bladder and at least one opening through which the air bladder is connectable to a source of oscillating pneumatic pressure, and
    a second portion adapted to be positioned in back of the patient's torso, the first and second portions being separate vest pieces,
    the first and second portions each having a bottom portion, the bottom portion of the second portion being configured to wrap around sides of the patient beneath the patient's arms and to detachably couple to the bottom portion of the first portion, the length of the bottom portion of the second portion being greater than the length of the bottom portion of the first portion,
    the first and second portions each having a pair of shoulder straps, the pair of shoulder straps of the second portion being detachably coupleable to the pair of shoulder straps of the first portion, the length of the shoulder straps of the second portion from a top edge of the second portion being greater than the length of the shoulder straps of the first portion from a top edge of the first portion,
    the air bladder being adapted to be positioned over a portion of the patient's rib cage and to avoid engaging at least a substantial portion of the patient's abdomen so that compression of the patient's abdomen is avoided during application of oscillating pneumatic pressure to the patient's torso by the air bladder.

2. The vest of claim 1, wherein the length of the bottom portion of the second portion is sufficient to wrap around the patient's sides and extend to the front of the patient's torso to detachably couple to the bottom portion of the first portion in the front of the patient' torso.

3. The vest of claim 1, wherein the lengths of the shoulder straps of the second portion are sufficient to extend over the patient's shoulders to the front of the patient's torso to detachably couple to the shoulder straps of the first portion in the front of the patient' torso.

4. The vest of claim 1, wherein the shoulder straps of the second portion are angled outwardly.

5. The vest of claim 1, wherein the air bladder engages less than about 75% of the circumference of the torso of the patient.

6. The vest of claim 1, wherein the air bladder is removable from the first portion.

7. The vest of claim 1, wherein the air bladder is integral with the first portion.

8. The vest of claim 1, wherein the air bladder is comprised of pleated material.

9. The vest of claim 1, wherein a top edge of the air bladder is positionable near a collarbone of the patient.

10. The vest of claim 1, wherein the air bladder is comprised of non-stretchable material.

11. The vest of claim 1, wherein the first portion is comprised of non-stretchable material.

12. The vest of claim 1, wherein the second portion is comprised of non-stretchable material.

13. The vest of claim 1, further comprising a pair of vertical stiffeners coupled to the second portion such that each vertical stiffener is generally aligned with an associated shoulder strap of the second portion.

14. The vest of claim 1, further comprising a horizontal stiffener coupled to the second portion near a bottom edge thereof.

15. The vest of claim 1, further comprising a pair of vertical stiffeners coupled to the first portion adjacent to side edges thereof.

16. The vest of claim 1, further comprising a horizontal stiffener coupled to the first portion near a bottom edge thereof.

17. The vest of claim 16, wherein the vertical stiffeners are malleable by hand.

18. The vest of claim 1, further comprising a handgrip attached to the second portion.

19. The vest of claim 18, wherein the handgrip angles downwardly from a bottom edge of the second portion.

20. The vest of claim 1, further comprising fasteners coupled to the first and second portions, the fasteners interacting to detachably couple the first and second portions together.

21. The vest of claim 20, wherein the fasteners comprise hook and loop fasteners.

22. The vest of claim 1, wherein oscillating pneumatic pressure applied to the air bladder from the source of oscillating pneumatic pressure has a frequency between about 5 Hertz and about 25 Hertz.

23. A pneumatic chest compression vest comprising:

a first portion adapted to be positioned in front of a patient's torso, the first portion having an air bladder and at least one opening through which the air bladder is connectable to a source of oscillating pneumatic pressure, a second portion adapted to be positioned in back of the patient's torso, the first and second portions being separate vest pieces, the first and second portions each having a bottom portion, the bottom portion of the second portion being configured to wrap around sides of the patient beneath the patient's arms and to detachably couple to the bottom portion of the first portion, the first and second portions each having a pair of shoulder straps, the pair of shoulder straps of the first portion being detachably coupleable to the pair of shoulder straps of the second portion, and a pair of vertical stiffeners coupled to the second portion such that each stiffener is generally aligned with an associated shoulder strap of the second portion, the air bladder being adapted to be positioned over a portion of the patient's rib cage and to avoid engaging at least a substantial portion of the patient's abdomen so that compression of the patient's abdomen is avoided during application of oscillating pneumatic pressure to the patient's torso by the air bladder.

24. The vest of claim 23, wherein the length of the bottom portion of the second portion is greater than the length of the bottom portion of the first portion.

25. The vest of claim 24, wherein the length of the bottom portion of the second portion is sufficient to wrap around the patient's sides and extend to the front of the patient's torso to detachably couple to the bottom portion of the first portion in the front of the patient' torso.

26. The vest of claim 23, wherein the length of the shoulder straps of the second portion from a top edge of the second portion is greater than the length of the shoulder straps of the first portion from a top edge of the first portion.

27. The vest of claim 26, wherein the lengths of the shoulder straps of the second portion are sufficient to extend over the patient's shoulders to the front of the patient's torso to detachably couple to the shoulder straps of the first portion in the front of the patient' torso.

28. The vest of claim 23, wherein the shoulder straps of the second portion are angled outwardly.

29. The vest of claim 23, further comprising a horizontal stiffener coupled to the second portion near a bottom edge thereof.

30. The vest of claim 23, further comprising a pair of vertical stiffeners coupled to the first portion adjacent to side edges thereof.

31. The vest of claim 23, further comprising a horizontal stiffener coupled to the first portion near a bottom edge thereof.

32. The vest of claim 23, further comprising a handgrip attached to the second portion.

33. The vest of claim 32, wherein the handgrip angles downwardly from a bottom edge of the second portion.

34. The vest of claim 23, further comprising fasteners coupled to the first and second portions, the fasteners interacting to detachably couple the first and second portions together.

35. The vest of claim 23, wherein oscillating pneumatic pressure applied to the air bladder from the source of oscillating pneumatic pressure has a frequency between about 5 Hertz and about 25 Hertz.

* * * * *